United States Patent
Stoeckel et al.

(10) Patent No.: US 8,686,728 B2
(45) Date of Patent: Apr. 1, 2014

(54) SYSTEM FOR ADAPTING AN RF TRANSMISSION MAGNETIC FIELD FOR IMAGE ACQUISITION

(75) Inventors: Bernd Stoeckel, Brooklyn, NY (US); Stefan Röll, Hirschaid (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 458 days.

(21) Appl. No.: 13/187,570

(22) Filed: Jul. 21, 2011

(65) Prior Publication Data

US 2013/0021033 A1 Jan. 24, 2013

(51) Int. Cl.
 *G01V 3/00* (2006.01)
(52) U.S. Cl.
 USPC .......................................... 324/318; 324/322
(58) Field of Classification Search
 USPC .................. 324/318, 322, 307, 309, 312, 314
 See application file for complete search history.

(56) References Cited

U.S. PATENT DOCUMENTS

| | | | |
|---|---|---|---|
| 5,001,428 A * | 3/1991 | Maier et al. | 324/309 |
| 7,002,347 B2 | 2/2006 | Feiweier et al. | |
| 7,259,562 B2 * | 8/2007 | Wang et al. | 324/318 |
| 2011/0309832 A1 | 12/2011 | Alagappan et al. | |
| 2013/0278262 A1 * | 10/2013 | Zhai et al. | 324/309 |

* cited by examiner

*Primary Examiner* — Louis Arana
(74) *Attorney, Agent, or Firm* — Peter R. Withstandley

(57) ABSTRACT

A system generates a Radio Frequency (RF) magnetic field in an MR imaging unit using an RF transmitting coil for generating a Radio Frequency (RF) magnetic field and multiple RF receiver coils for receiving RF signals for Magnetic Resonance (MR) image data acquisition. An RF transmission coil generates an RF magnetic field. An RF receiver coil receives an RF signal for MR image data acquisition and couples a magnetic field from the RF receiver coil to the RF transmission coil for adaptively altering the RF magnetic field generated by the RF transmission coil to reduce inhomogeneity in the RF magnetic field generated by the RF transmission coil in response to applying an RF pulse to the RF transmission coil. An adjustment processor adjusts characteristics of the RF receiver coil to alter the RF magnetic field generated by the RF transmission coil.

17 Claims, 12 Drawing Sheets

SYSTEM FOR ADAPTING AN RF TRANSMISSION MAGNETIC FIELD FOR IMAGE ACQUISITION

FIELD OF THE INVENTION

This invention concerns an MR imaging system for reducing inhomogeneity in an RF magnetic field generated by an RF transmission coil using one or more RF receiver coils by coupling a magnetic field from the RF receiver coils to the RF transmission coil.

BACKGROUND OF THE INVENTION

In Magnetic Resonance Image (MRI) scanners employing multiple RF (Radio frequency) receiver coils in arrays, an increase in static homogenous field ($B_0$) strength from 1.5 Tesla (T) to 3 T and 7 T and beyond causes increasing non-uniformity in RF magnetic excitation fields ($B_1$) generated by an RF transmit coil. Further, it is desirable to be able to control the transmitted RF magnetic field spatially with greater precision and individually for different patients, e.g. to produce a more homogenous RF magnetic field within a large Field of View (FOV) or to focus on a reduced, smaller FOV. A smaller FOV reduces image acquisition time and enables acquisition of an image of a reduced FOV with higher pixel resolution. A system according to invention principles addresses these problems and requirements and associated problems.

SUMMARY OF THE INVENTION

A system uses modified parallel RF receiver coil array arrangements to modify a magnetic field generated by a transmit coil employed in MR imaging by adapting a magnetic field (B1) generated by a global transmit coil in amplitude and phase to increase or decrease a local B1 field for use in B1 Shimming and fast selective RF pulses, for example. A system generates a Radio Frequency (RF) magnetic field in an MR imaging unit using an RF transmitting coil for generating a Radio Frequency (RF) magnetic field and multiple RF receiver coils for receiving RF signals for Magnetic Resonance (MR) image data acquisition. An RF transmission coil generates an RF magnetic field. An RF receiver coil receives an RF signal for MR image data acquisition and couples a magnetic field from the RF receiver coil to the RF transmission coil for adaptively altering the RF magnetic field generated by the RF transmission coil to reduce inhomogeneity in the RF magnetic field generated by the RF transmission coil in response to applying an RF pulse to the RF transmission coil. An adjustment processor adjusts characteristics of the RF receiver coil to alter the RF magnetic field generated by the RF transmission coil.

DETAILED DESCRIPTION OF THE INVENTION

A system uses modified parallel RF receiver coil array arrangements to modify a magnetic field generated by a transmit coil employed in MR imaging. The excitation radio frequency (RF) magnetic field (B1) generated by a global transmit coil in an MR imaging device is modulated in amplitude and phase by parallel local RF receiver coils. The receiver coil arrangements are not only used for signal reception but advantageously contain additional functionality enabling either increase or decrease of a local B1 field for use in B1 Shimming and fast selective RF pulses, for example. The system couples a magnetic field from an MR RF receiver coil array to an MR RF transmit coil during excitation of the MR RF transmit coil to adjust an RF excitation magnetic field (B1) in performing image data acquisition. The system enables local modulations of the B1 field, without the requirement of introducing an expensive parallel transmit (pTX) system comprised of several additional parallel signal modulators combined with high power RF power amplifiers and a dedicated pTX transmit coil, for example. The system reduces cost, and potential patient discomfort.

Figure 1:
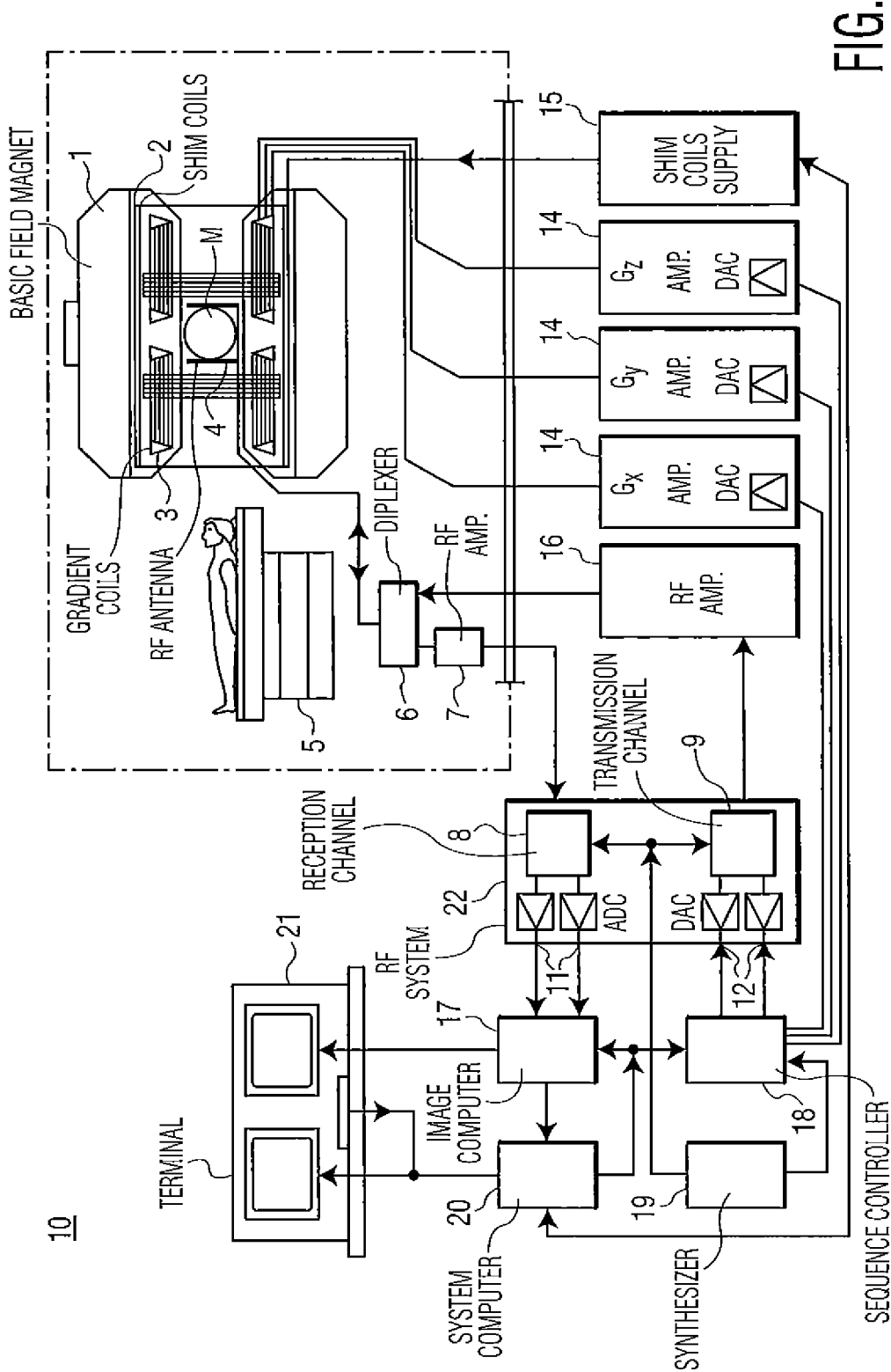
FIG. 1 shows an MR imaging unit using a system for generating a Radio Frequency (RF) magnetic field, according to invention principles.

FIG. 1 shows an MR imaging unit 10 including a system for generating a Radio Frequency (RF) magnetic field. A basic field magnet 1 generates a strong magnetic field, which is constant in time, for the polarization or alignment of the nuclear spins in the examination region of an object, such as, for example, a part of a human body to be examined. The high homogeneity of the basic magnetic field (B0) required for the magnetic resonance measurement is provided in a spherical measurement volume M, for example, into which the parts of the human body to be examined are brought. In order to satisfy the B0 homogeneity requirements and especially for the elimination of time-invariant influences, shim-plates made of ferromagnetic material are mounted at suitable positions. Time-variable influences are eliminated by shim coils 2, which are controlled by a shim-current supply 15.

In the basic magnetic field 1, a cylinder-shaped gradient coil system 3 is used, which consists of three windings, for example. Each winding is supplied with current by an amplifier 14 in order to generate a linear gradient field in the respective directions of the Cartesian coordinate system. The first winding of the gradient field system 3 generates a gradient $G_x$ in the x-direction, the second winding generates a gradient $G_y$ in the y-direction, and the third winding generates a gradient $G_z$ in the z-direction. Each amplifier 14 contains a digital-analog converter, which is controlled by a sequence controller 18 for the generation of gradient pulses at proper times.

Figure 2:
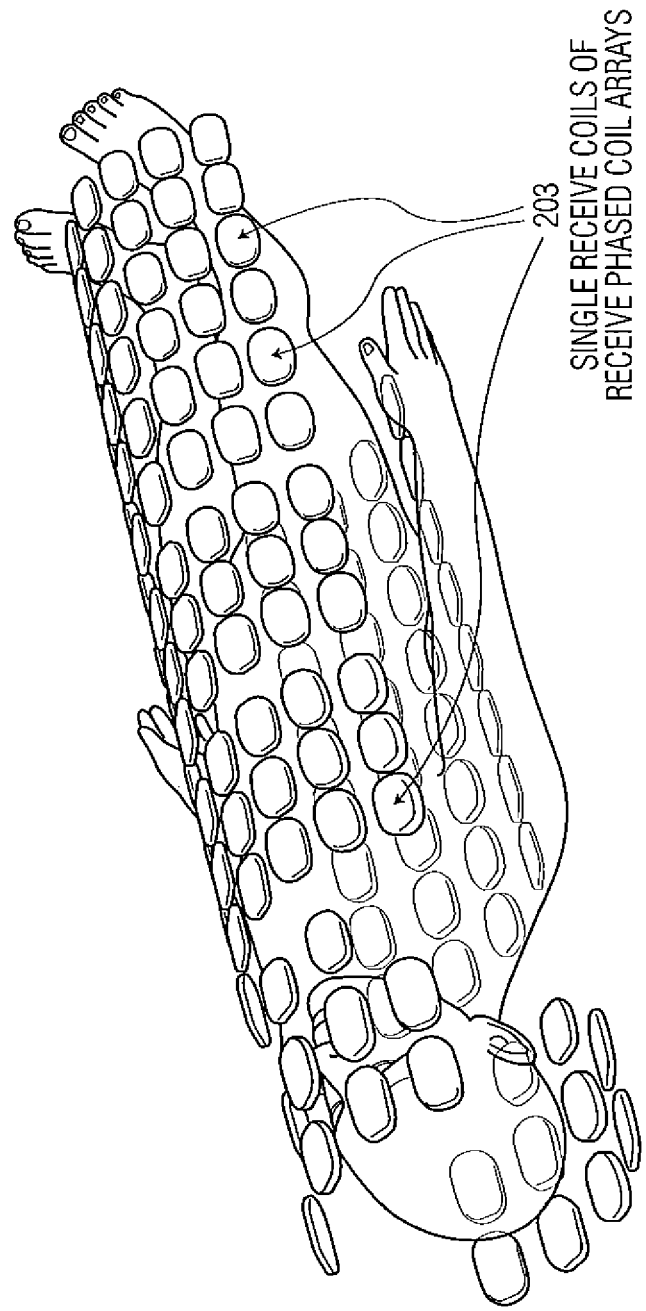
FIG. 2 shows a RF receiver coil array close to a body including a spine array or cardiac array, according to invention principles.
Figure 3:
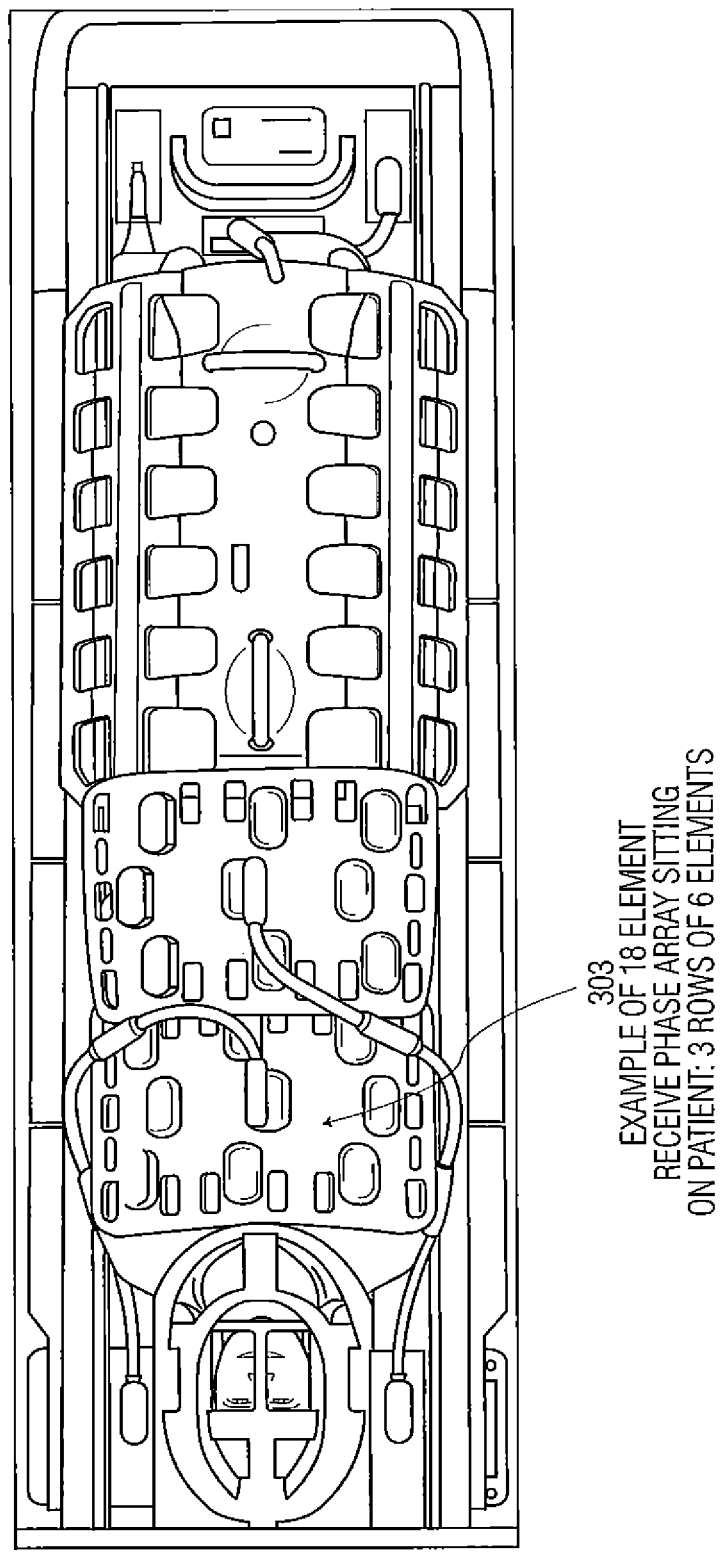
FIG. 3 shows an 18 element RF receiver coil array close to a body, according to invention principles.

Within the gradient field system 3, a radio-frequency (RF) transmission coil is located which converts the radio-frequency pulses emitted by a radio-frequency power amplifier 16 via multiplexer 6 into a magnetic alternating field in order to excite the nuclei and align the nuclear spins of the object to be examined or the region of the object to be examined. A standard integrated RF transmit body coil is used for transmitting (generation of B1 excitation field). In one embodiment, RF receiver coils 4 comprise a subset or substantially all of, multiple RF coils arranged in sections along the length of volume M corresponding to the length of a patient. FIG. 2 shows an RF receiver coil array close to a body including a spine array and cardiac array comprising multiple individual RF receiver coil elements including elements 203, for example. FIG. 3 shows an 18 element RF receiver coil chest array 303 close to a body. System 10 advantageously uses receiver array coils for both MR RF signal reception and also for modulation of MR RF signal transmission An individual section RF coil of coils 4 comprises multiple RF coils providing RF image data that is used in parallel to generate a single MR image. RF pulse signals are applied to RF coils 4, which in response produces magnetic field pulses which rotate the spins of the protons in the imaged body by ninety degrees or by one hundred and eighty degrees for so-called "spin echo" imaging, or by angles less than or equal to 90 degrees for so-called "gradient echo" imaging. In response to the applied RF pulse signals, RF coils 4 receive MR signals, i.e., signals from the excited protons within the body as they return to an equilibrium position established by the static and gradient magnetic fields. The MR signals comprising nuclear spin echo signals received by RF coils 4 as an alternating field resulting from the precessing nuclear spins, are converted into a voltage that is supplied via an amplifier 7 and multiplexer 6 to a radio-frequency receiver processing unit 8 of a radio-frequency system 22. The radio-frequency system 22 operates in an RF signal transmission mode to excite protons and in a receiving mode to process resulting RF echo signals.

RF receiver coils 4 receive an RF signal for MR image data acquisition and are magnetically coupled to the RF transmission coil for adaptively altering the RF magnetic field generated by the RF transmission coil to reduce inhomogeneity in the RF excitation magnetic field (B1) generated by the RF transmission coil in response to applying an RF pulse to the RF transmission coil. RF receiver coils 4 are magnetically coupled to the RF transmission coil to adaptively alter the magnetic field generated by the transmission coil. An adjustment processor in system computer 20 adjusts characteristics of RF receiver coils 4 to alter the RF magnetic field generated by the transmission coil.

Figure 5:
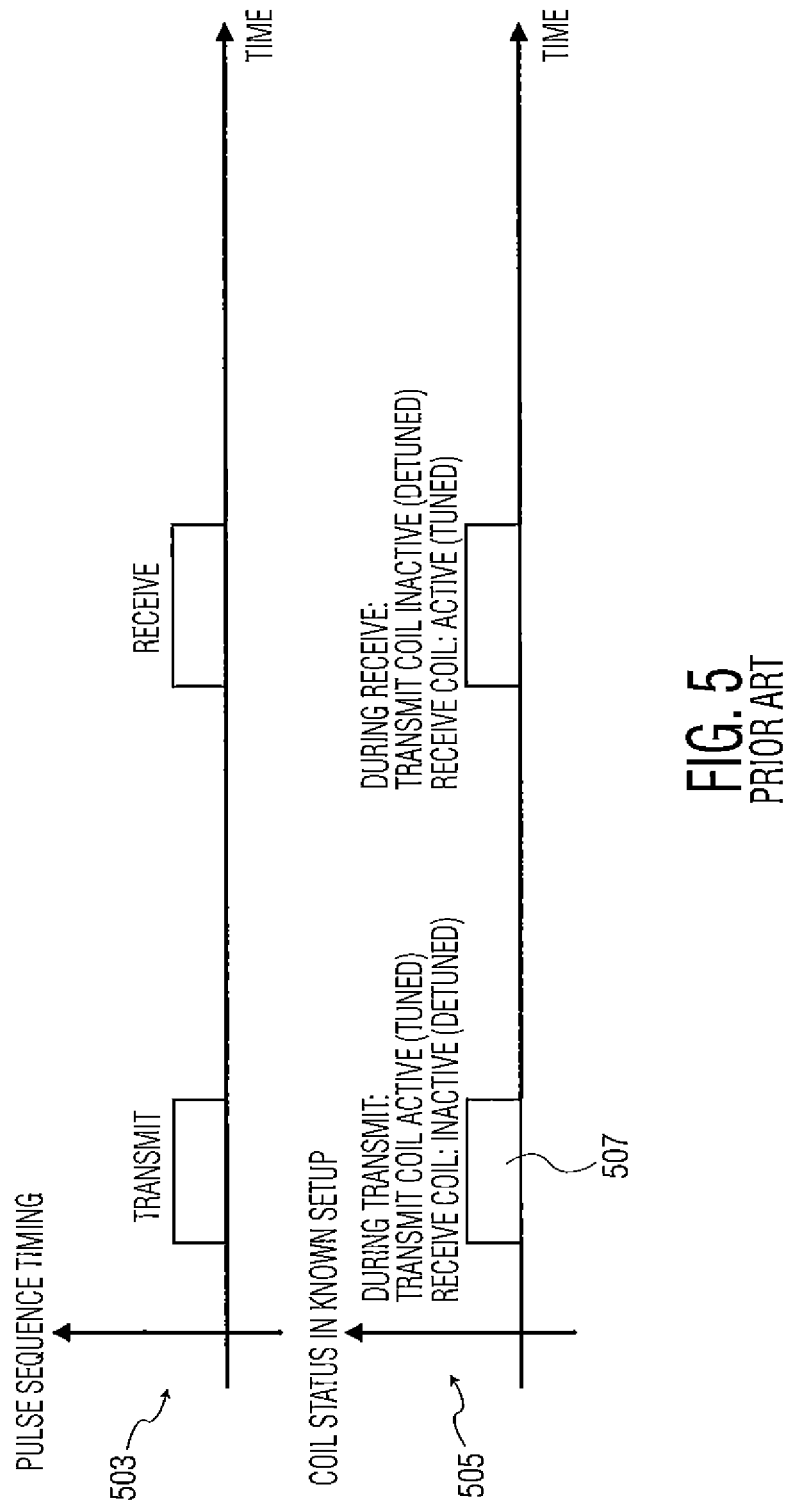
FIG. 5 shows a known RF transmission and receiver coil activation sequence and associated coil status.
Figure 6:
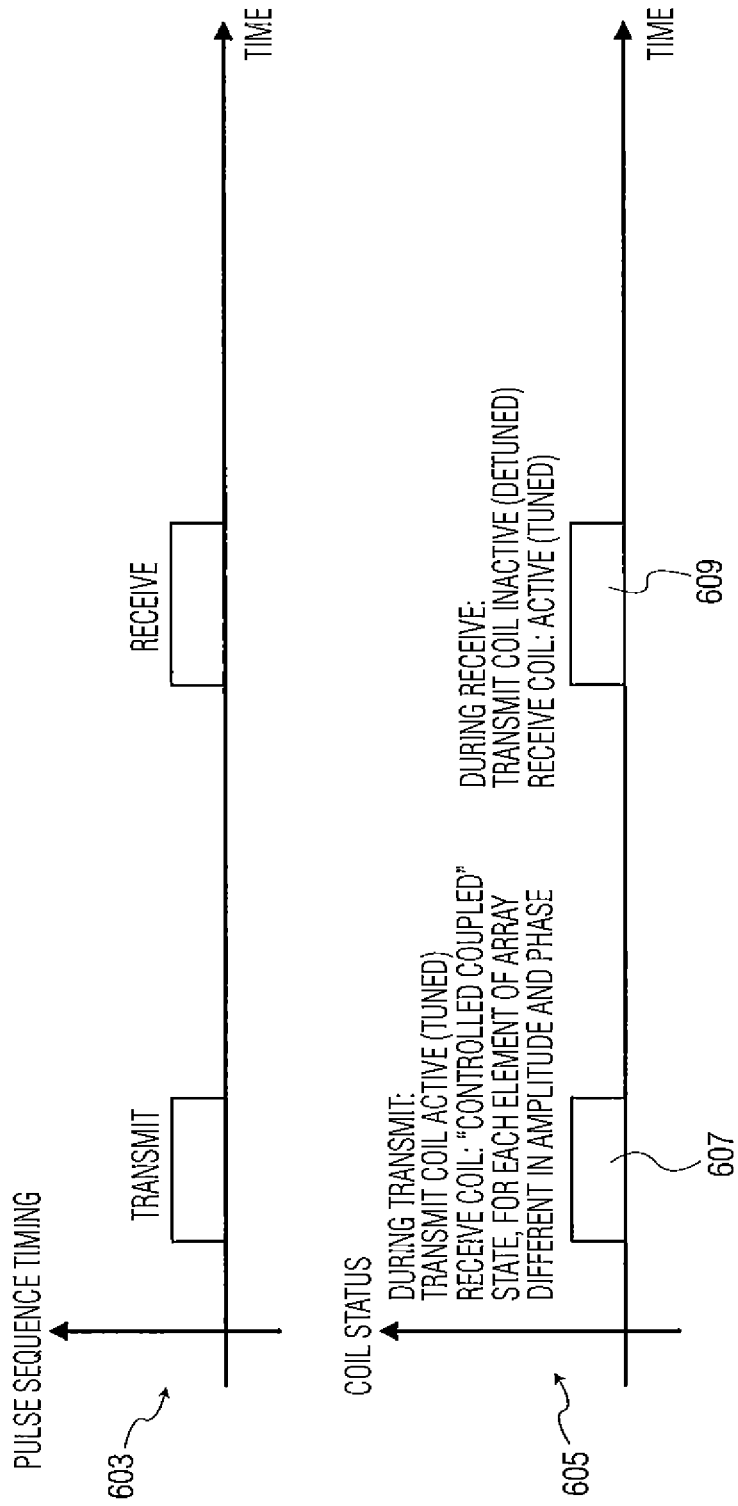
FIG. 6 shows an RF transmission and receiver coil activation sequence and associated coil status, according to invention principles.

FIG. 6 shows an RF transmission pulse sequence and receiver coil activation sequence 603 and associated coil status 605 used by system 10 (FIG. 1). In performing MR imaging, during RF pulse transmission interval 607 a global transmit (Tx) coil ("body coil") is activated (tuned) and transmitting in response to an applied pulse, active or passive elements in individual coils of RF receiving coil unit 4 are switched into individual coils to tune or detune the coils in order to bring the individual coils partially in resonance, which advantageously amplifies or attenuates a local B1 field being generated according to coil sensitivity profiles of the receiver (Rx) coil elements. An individual RF receiver coil element of RF receiver coils 4 is in a coupling controlled state in which phase and amplitude of coupling with a transmission coil is controlled. The Rx coil element sensitivities are determined by a patient specific configuration performed automatically by system 10 or in response to user command. During RF receive interval 609, the transmission coil is inactivated (detuned) and the RF receive coils 4 are active (tuned). In contrast, FIG. 5 shows a pulse sequence indicating a known RF transmission and receiver coil activation sequence 503 and associated coil status 505. In the known sequence, a global transmit (Tx) coil is activated (tuned) in interval 507 during which RF receiving coils are inactivated (detuned).

In system 10 (FIG. 1) during RF transmission via the transmission coil, elements of the receiver coil 4 phased array are not inactive and detuned as in known systems but are activated and in a new status. An individual RF receiver coil element of the receive array 4 couples to the transmit coil in a controlled manner, whereby the coupling is adaptively changed for individual coils and in time to accommodate change in B1 field. The transmit coil induces a current in individual RF receive coil elements and the current is individually controlled in amplitude and phase (within predetermined constraints) by control of the resonant frequency of each individual RF receiver coil. During a receive period, the transmit coil is inactivated (detuned) and elements of the receive array are active (tuned).

Figure 7:
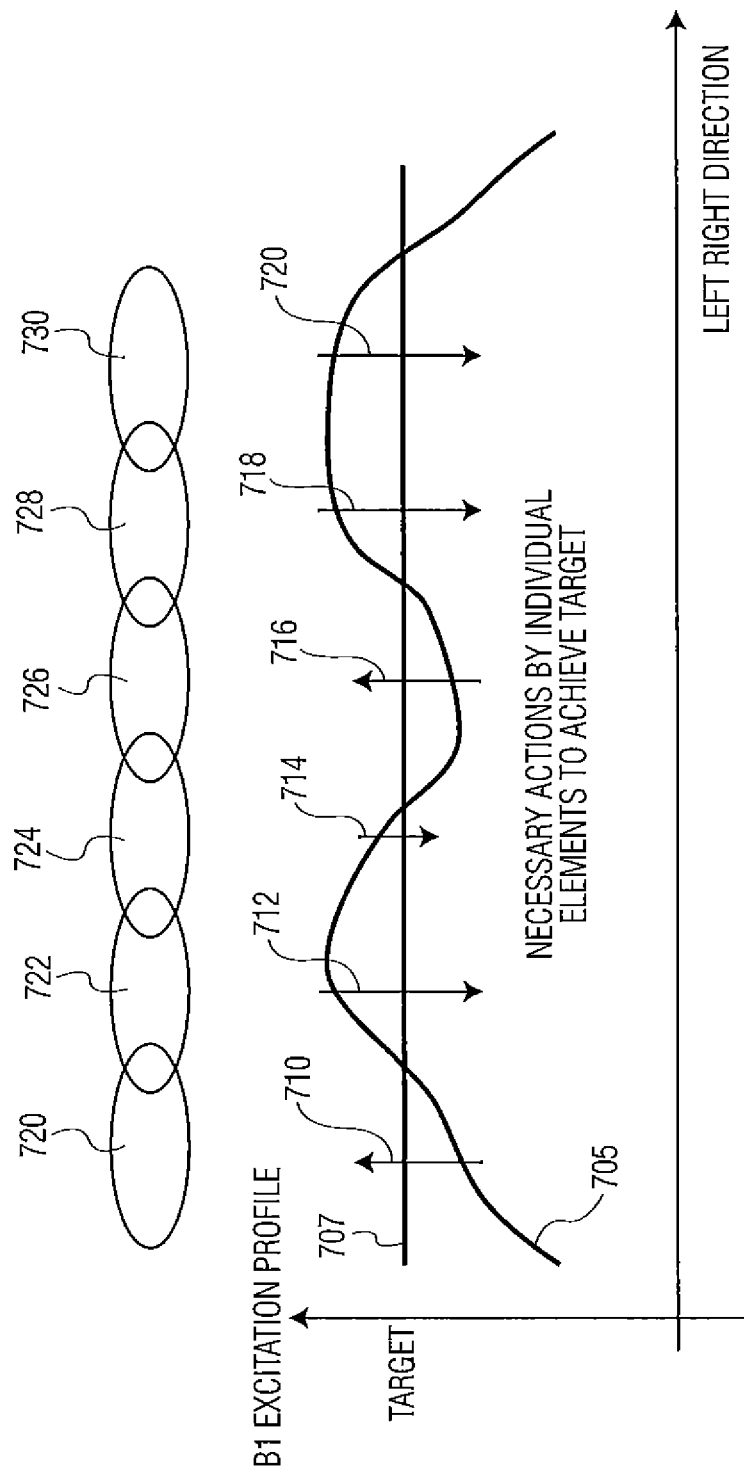
FIG. 7 illustrates variation in an RF excitation magnetic field (B1) received by multiple RF coils across a patient body, according to invention principles.

FIG. 7 illustrates variation in an RF excitation magnetic field (B1) generated by system 10 (FIG. 1) received by multiple RF coils across a patient body. A row of six receiver coil elements 720, 722, 724, 726, 728 and 730 of an array of receive elements positioned across a patient body receive a magnetic field as indicated in curve 705. The x-axis comprises length across a patient body (left to right) and the y-axis indicates RF magnetic excitation fields ($B_1$) (in microTesla). In order to improve homogeneity of the RF excitation magnetic field, system 10 increases field 710 seen by coil 720, reduces field 712 seen by coil 722, reduces field 714 seen by coil 724, increases field 716 seen by coil 726, reduces field 718 seen by coil 728 and reduces field 720 seen by coil 730. System 10 advantageously generates a B1 magnetic field of improved homogeneity, by adaptively adjusting magnetic field coupled from an RF transmit coil to RF receiver coils 720-730 to reduce wave propagation disturbance effects (sometimes referenced as dielectric resonances) which distort the B1 field in tissue. In an alternative approach the system advantageously accelerates image acquisition by enabling local modulation of a reduced field of view (FOV) that is imaged and improves resolution of the reduced FOV. The system takes advantage of the spatial location of the typical parallel array coils being close to the patient to adjust an RF magnetic field to a desired value by adjusting both amplitude and phase characteristics of the magnetic field coupled from a receiver coil array to a transmit coil to adapt the RF magnetic field within the patient.

Figure 4:
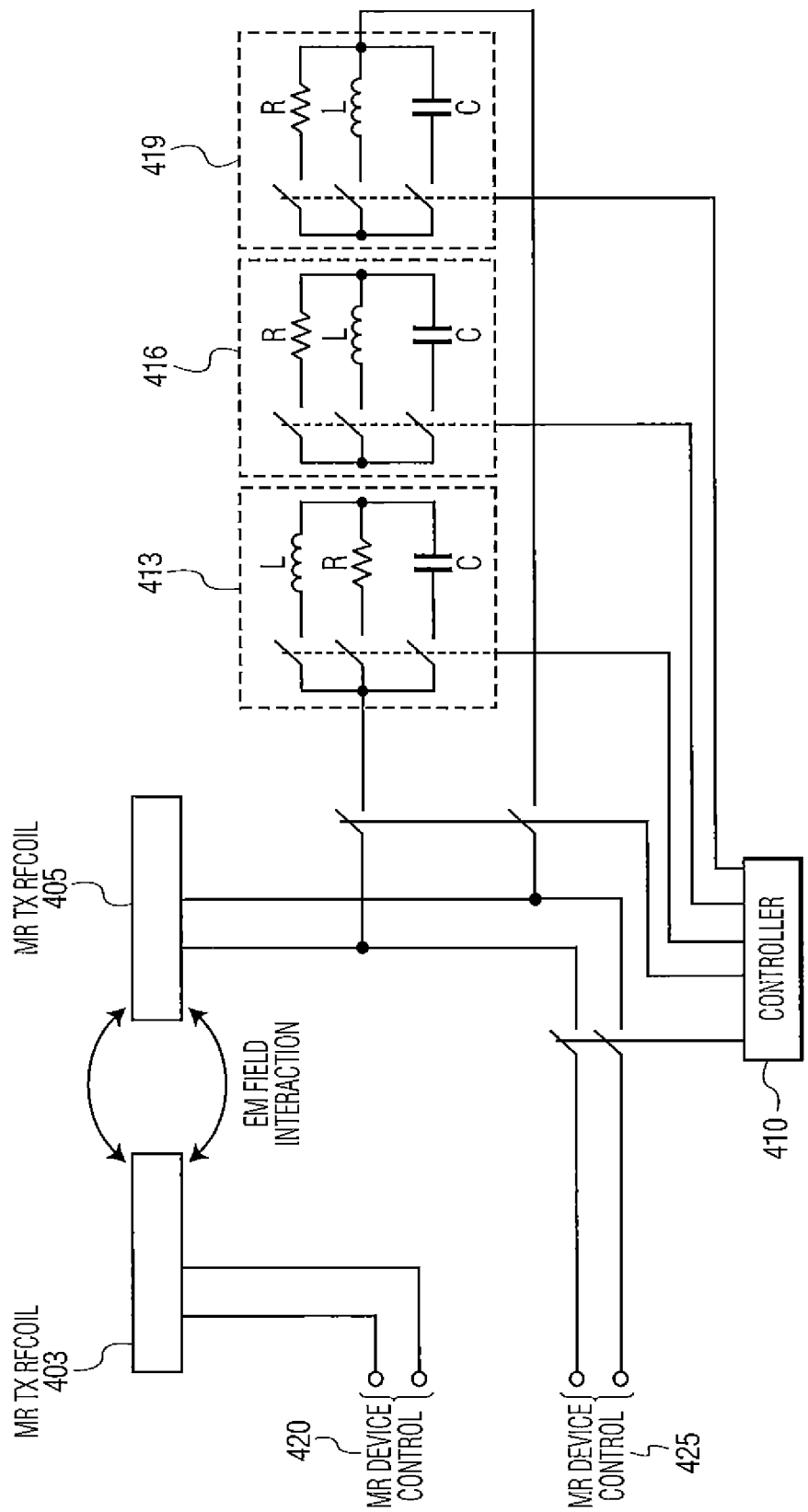
FIG. 4 shows an RF receiver coil control circuit used for adaptively adjusting a Radio Frequency (RF) magnetic field, according to invention principles.
Figure 10:
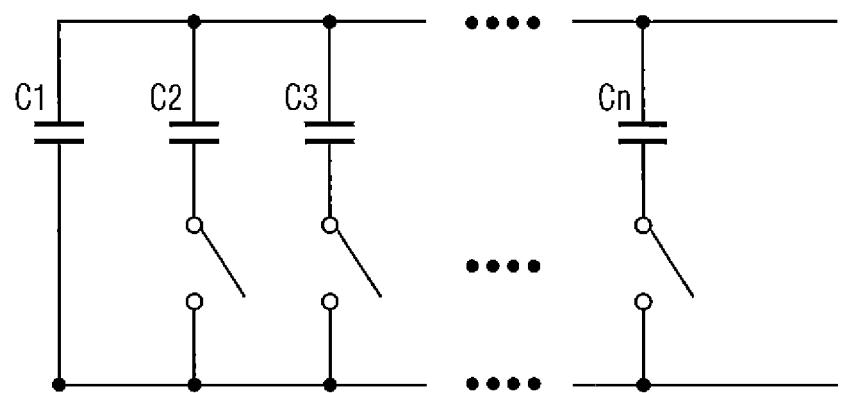
FIG. 10 shows RF receiver coil control circuit elements for adaptively adjusting a Radio Frequency (RF) magnetic field, according to invention principles.

FIG. 4 shows an RF receiver coil control circuit for controlling an individual coil of coil array 4 (FIG. 1) for adaptively adjusting a Radio Frequency (RF) magnetic field. Controller 410 in system computer 20 (FIG. 1) controls the electrical characteristics of receiver coil 405 by adaptively selecting and switching in a series and/or parallel combination of different passive elements to complete a coil circuit with resonance or off-resonance properties as needed. In one embodiment, the elements comprise inductance, capacitance or resistance, (L, C, R) components. In another embodiment, active elements may be used such as voltage controlled capacitance, inductance or resistance elements. FIG. 10 shows RF receiver coil control circuit capacitance elements (but in other embodiments may be inductance or resistance elements or combinations of L, C, R elements) that may be selectively switched in to achieve a desired capacitance value using electronic switches for adjusting coil properties and adaptively adjusting a transmission RF magnetic field. Individual components of parallel element combinations 413, 416 and 419 may be selectively incorporated or bypassed to form a component series 413, 416 and 419.

A parallel element combination may comprise more than three elements enabling selection of particular values of an inductance, capacitance or resistance. Alternatively voltage controlled capacitance (e.g., a varactor), inductance or resistance elements may be used enabling controller 410 to adaptively select a desired component value and desired parallel and series combination of L, C, R values to adjust electrical characteristics of receiver coil 405. Controller 410 adjusts electrical characteristics of receiver coil 405 to improve homogeneity of an RF excitation magnetic field (B1) by adaptively adjusting magnetic field coupling from RF receiver coil 405 to RF transmission coil 403. RF transmission coil 403 is connected to MR system pulse generation and control via terminals 420 for generating an RF excitation field. Similarly, RF receiver coil 405 is connected to the MR system via terminals 425 for acquisition of RF image data acquisition in response to the RF excitation field.

Figure 8:
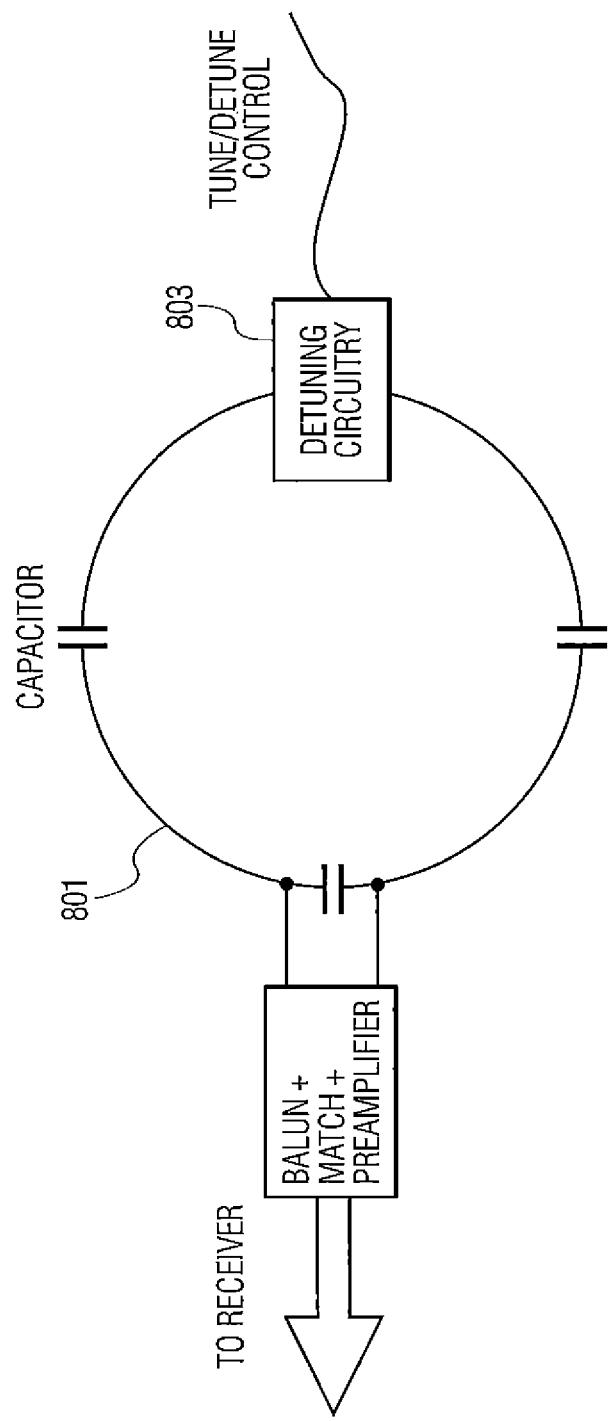
FIG. 8 shows a known individual RF receiver coil element of a receiver coil array.
Figure 9:
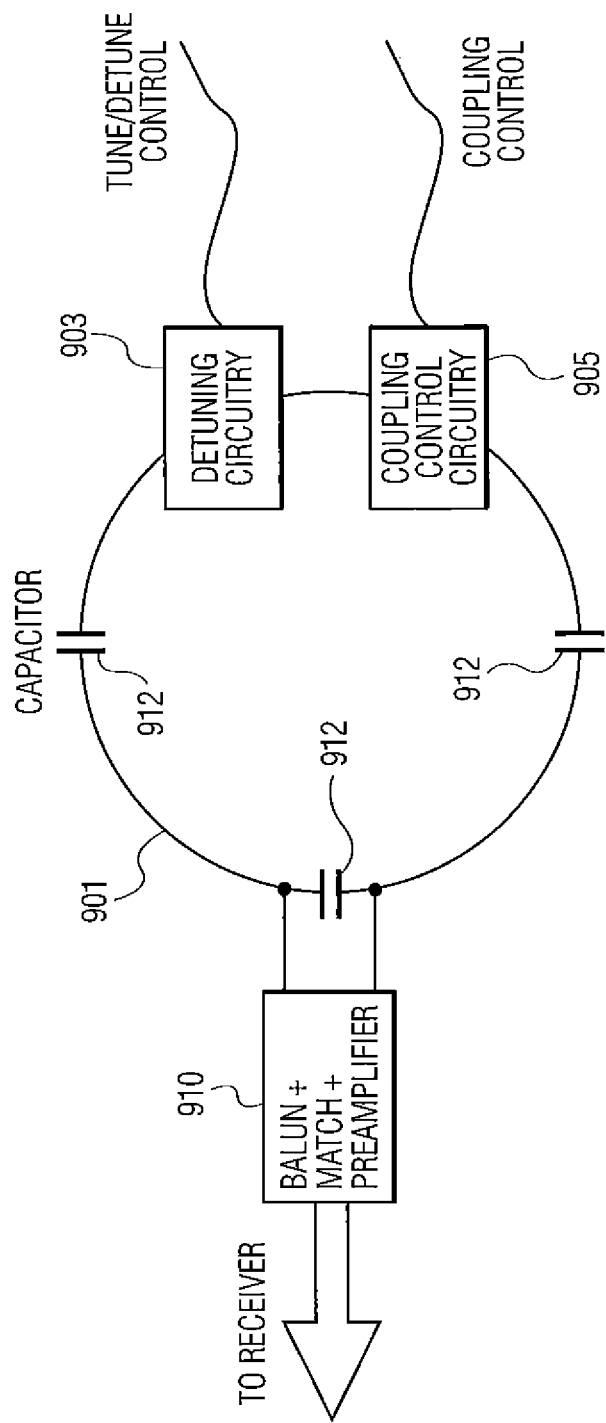
FIG. 9 shows an individual RF receiver coil element having adaptive resonance characteristics magnetically coupled to an RF transmission coil during transmission, according to invention principles.

FIG. 9 shows an individual RF receiver coil element 901 having adaptive resonance characteristics. Coil 901 including series capacitors 912, is magnetically coupled to an RF transmission coil during transmission. Coupling control unit 905 such as the unit of FIG. 4, during transmission by a transmission coil, adaptively selects and switches in a series and/or parallel combination of different L, C, R elements (and/or adaptively selects L, C, R element values via voltage control, for example) to complete a coil circuit with desired resonance or off-resonance properties to adapt field B1 produced by the transmission coil. The detuning unit 903 permits inactivation of receiver coil 901 but does not inactivate coil 901 during RF transmission by the transmission coil. Interface circuit 910 including a balun, pre-amplifier and impedance match, processes a signal derived across a series capacitor 912 of coil 901 and provides a receiver coil signal for MR signal processing system 10 (FIG. 1). In contrast, FIG. 8 shows a known individual RF receiver coil element 801 of a receiver coil array with detuning element 803 used to inactivate the receiver coil during RF transmission by the transmission coil. The known coil 801 does not include a unit such as unit 905 of FIG. 9.

Figure 11:
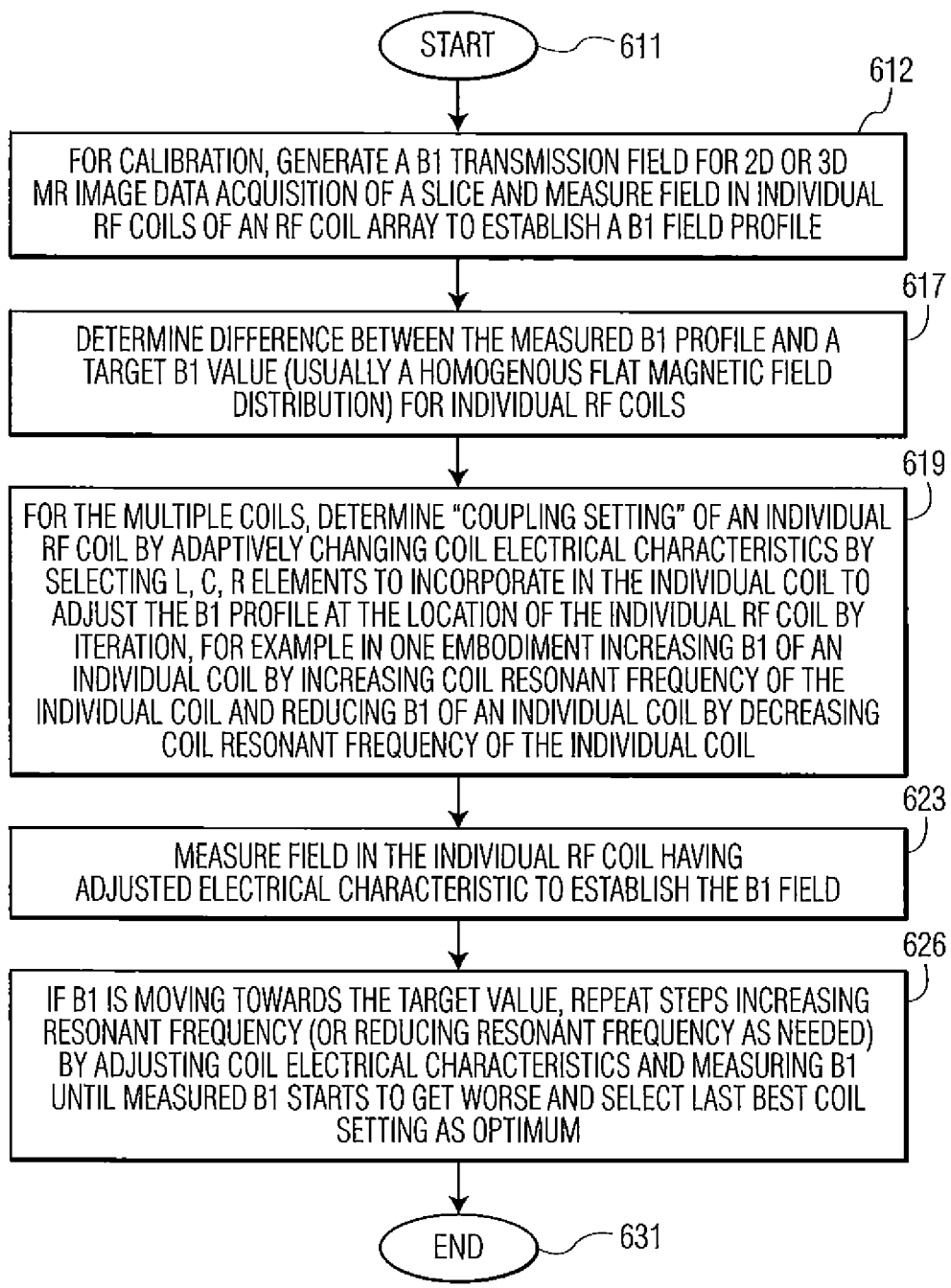
FIG. 11 shows a flowchart of a process for iteratively adjusting an RF excitation magnetic field (B1) received by individual RF coils of multiple RF coils across a patient body, according to invention principles.

FIG. 11 a flowchart of a process for iteratively adjusting an RF excitation magnetic field (B1) received by individual RF coils of multiple RF coils across a patient body. In step 612 following the start at step 611, in performing calibration, system 10 (FIG. 1) generates a B1 transmission field for 2D or 3D MR image data acquisition of a slice and measures a field in individual RF coils of RF coils 4 to establish a B1 field profile of each RF coil. In step 617 an adjustment processor determines a difference between the measured B1 profile and a target B1 value (e.g. a homogenous flat magnetic field distribution or a reduced FOV) for individual RF coils of coil array 4 (as illustrated in FIG. 7). In step 619, for the multiple coils of array 4, the adjustment processor determines "coupling setting" of an individual RF coil by adaptively changing coil electrical characteristics by selecting L, C, R elements to incorporate in the individual coil to adjust the B1 profile at the location of the individual RF coil by iteration. For example in one embodiment, the system increases B1 of an individual coil by increasing coil resonant frequency of the individual coil and alternatively, reduces B1 of an individual coil by decreasing coil resonant frequency of the individual coil.

In step 623, the adjustment processor measures a field in the individual RF coil having adjusted electrical characteristics to establish a B1 field. In step 626, if B1 is moving towards the target value, the adjustment processor repeats the process steps increasing resonant frequency of the individual coil (or reducing resonant frequency as needed) by adjusting coil electrical characteristics and measuring B1 until measured B1 starts to diverge from the target B1 value and selects the last best coil setting as optimum. In one embodiment, an increase in B1 field occurs in a coil in response to increasing coil resonant frequency above an MR resonant frequency because of capacitive coupling (positive feedback) and a decrease in B1 field occurs in a coil in response to reducing coil resonant frequency below an MR resonant frequency because of inductive coupling (negative feedback). The iterative procedure also accommodates interaction occurring between different RF receiver coil fields. The process of FIG. 11 terminates at step 631.

In another embodiment, the adjustment processor employs a look-up table to adjust electrical characteristics of a receiver coil in an array of M×N RF receiver coil elements to improve homogeneity of an RF excitation magnetic field (B1) by adaptively adjusting magnetic field coupling from an individual RF receiver coil to the RF transmission coil. The adjustment processor iteratively and incrementally adjusts electrical characteristics (e.g. via selection of incorporated L, C, R component combination values) of an individual coil in setting increments for a total of K different settings (covering frequency range from below MR frequency to above MR frequency) in a calibration pre-scan operation. The adjustment processor measures the resultant B1 field as a result of coupling between the individual receiver coil and the transmission coil. The adjustment processor performs these measurements for the M×N array for each of the K settings to determine a resultant B1 field and change in B1 field and stores the data in a lookup table. Thereby the adjustment processor provides data representing a 3D electromagnetic field simulation in a typical human body for the different potential coil characteristic settings and field coupling for M×N×K coil characteristic setting combinations.

Continuing with FIG. 1 operation, in transmission mode, system 22 (FIG. 1) transmits RF pulses via transmission channel 9 to initiate nuclear magnetic resonance in volume M. Specifically, system 22 processes respective RF echo pulses associated with a pulse sequence used by system computer 20 in conjunction with sequence controller 18 to provide a digitally represented numerical sequence of complex numbers. This numerical sequence is supplied as real and imaginary parts via digital-analog converter 12 in the high-frequency system 22 and from there to a transmission channel 9. In the transmission channel 9, the pulse sequences are modulated with a radio-frequency carrier signal, having a base frequency corresponding to the resonance frequency of the nuclear spins in the measurement volume M.

The conversion from transmitting to receiving operation is done via a multiplexer 6. RF coils 4 emit RF pulses to excite nuclear proton spins in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17. Imaging computer 17 reconstructs an image from the processed acquired RF echo pulse data. The processing of RF data, the image data and the control programs is performed under control of system computer 20. In response to predetermined pulse sequence control programs, sequence controller 18 controls generation of desired pulse sequences and corresponding scanning of k-space. In particular, sequence controller 18 controls the switching of the magnetic gradients at appropriate times, transmission of RF pulses with a determined phase and amplitude and reception of magnetic resonance signals in the form of RF echo data. Synthesizer 19 determines timing of operations of RF system 22 and sequence controller 18. The selection of appropriate control programs for generating an MR image and the display of the generated nuclear spin image is performed by a user via terminal (console) 21, which contains a keyboard and one or more screens. System 10 uses magnetic field gradients and radio frequency excitation to create an image. System computer 20 translates acquired k-space data onto a Cartesian grid and a Three-Dimensional Fourier Transform (3DFT) method is used to process the data to form a final image.

Figure 12:
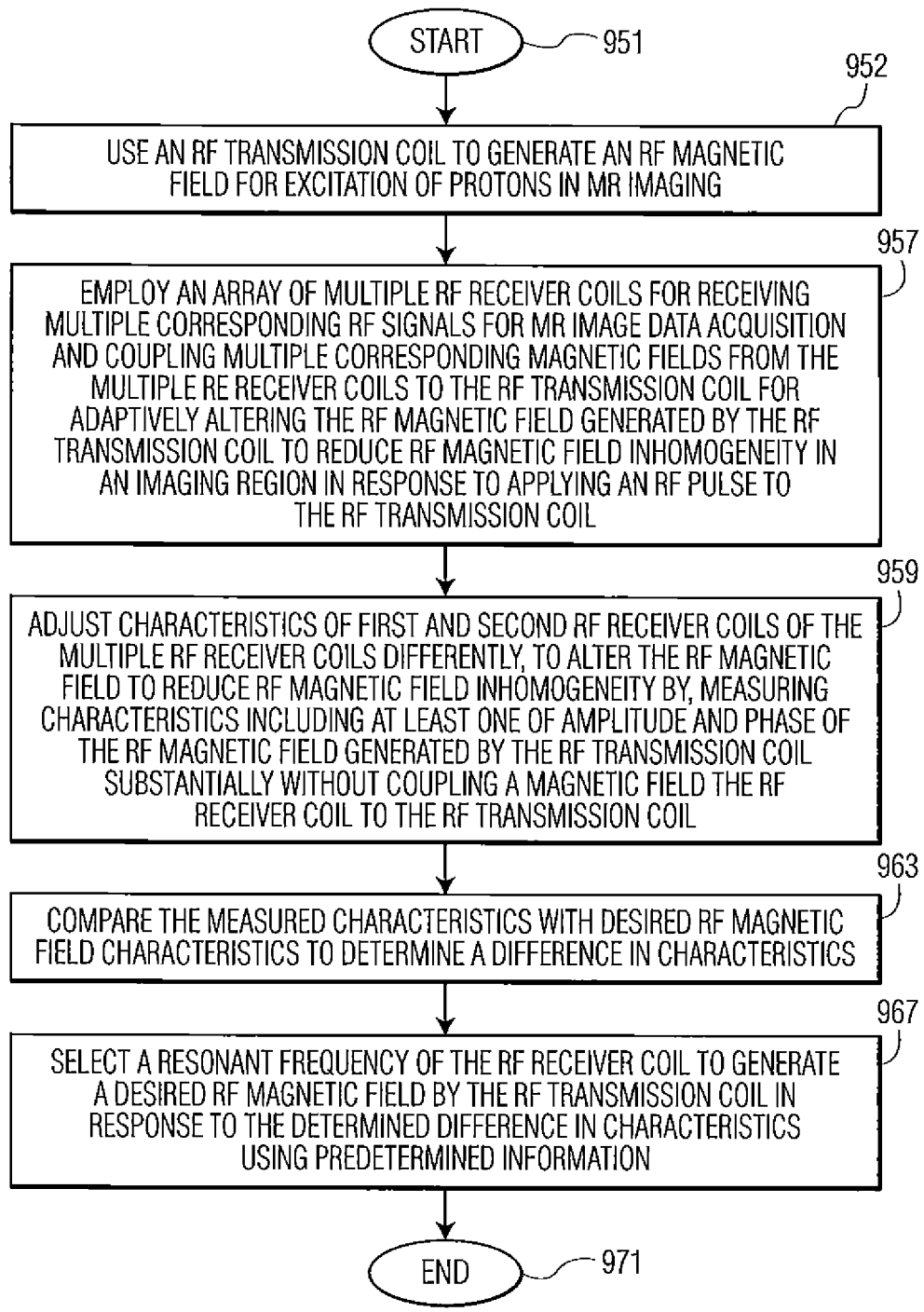
FIG. 12 shows a flowchart of a process performed by an MR imaging unit using a system for generating a Radio Frequency (RF) magnetic field, according to invention principles.

FIG. 12 shows a flowchart of a process performed by MR imaging system 10 (FIG. 1) using a system for generating a Radio Frequency (RF) magnetic field. In step 952 following the start at step 951, an RF transmission coil in system 10 generates an RF magnetic field. In step 957, array of multiple RF receiver coils 4 receives multiple corresponding RF signals for MR image data acquisition and are individually coupled to the RF transmission coil for adaptively altering the RF magnetic field generated by the RF transmission coil to reduce RF magnetic field inhomogeneity in an imaging region in response to applying an RF pulse to the RF transmission coil. Receiver coils 4 are coupled to the RF transmission coil to adaptively alter the RF magnetic field generated by the RF transmission coil to refine a field of view imaged by the MR imaging unit, for example.

In step 959, an adjustment processor adjusts characteristics of first and second RF receiver coils of the multiple RF receiver coils differently, to alter the RF magnetic field to reduce RF magnetic field inhomogeneity. The adjustment processor adjusts characteristics of RF receiver coils 4 by adaptively forming an individual RF receiver coil into a closed loop including at least one of, (a) a capacitor, (b) an inductor and (c) a resistor. The adjustment processor determines characteristics required for the RF receiver coil for use in adjusting characteristics of the RF receiver coil and adjusts the characteristics by connecting an electrical component to the RF receiver coil to form an RF receiver coil (e.g. comprising a closed loop) having a resonant frequency for coupling a magnetic field from the RF receiver coil to the RF transmission coil to adaptively alter the RF magnetic field generated by the RF transmission coil to a desired field strength. The processor adaptively alters amplitude and phase of the RF magnetic field generated by the RF transmission coil. The electrical component comprises at least one of, (a) a capacitor, (b) an inductor, (c) a resistor, (d) an electrically variable capacitance, (e) an electrically variable inductance and (f) an electrically variable resistance. The electrical component may also comprise a series combination of at least two of, (i) a capacitor, (ii) an inductor and (iii) a resistor.

The adjustment processor in step 959 determines the required characteristics by measuring characteristics including at least one of amplitude and phase of the RF magnetic field generated by the RF transmission coil substantially without coupling a magnetic field from the RF receiver coil to the RF transmission coil. In step 963 the adjustment processor compares the measured characteristics with desired RF magnetic field characteristics to determine a difference in characteristics. The adjustment processor in step 967 selects a resonant frequency of the RF receiver coil to generate a desired RF magnetic field by the RF transmission coil in response to the determined difference in characteristics using predetermined (e.g., lookup table) information. The predetermined information comprises predetermined mapping information associating RF receiver coil resonant frequency with corresponding changes in RF transmission coil magnetic field characteristics. The process of FIG. 12 terminates at step 971.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-12 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system adaptively adjusts an RF excitation magnetic field (B1) generated by a transmit coil employed in MR imaging by coupling a magnetic field from an MR RF receiver coil array to the transmit coil in performing image data acquisition. Further, the processes and applications may, in alternative embodiments, be located on one or more (e.g., distributed) processing devices on a network linking the units of FIG. 1. Any of the functions and steps provided in FIGS. 1-12 may be implemented in hardware, software or a combination of both.

What is claimed is:

1. In an MR imaging unit using an RF transmitting coil for generating a Radio Frequency (RF) magnetic field and a plurality of RF receiver coils for receiving RF signals for Magnetic Resonance (MR) image data acquisition, a system for generating a Radio Frequency (RF) magnetic field comprising:
    an RF transmission coil for generating an RF magnetic field;
    an RF receiver coil for receiving an RF signal for MR image data acquisition and coupling a magnetic field from said RF receiver coil to said RF transmission coil for adaptively altering said RF magnetic field generated by said RF transmission coil to reduce inhomogeneity in said RF magnetic field generated by said RF transmission coil in response to applying an RF pulse to said RF transmission coil; and
    an adjustment processor for adjusting characteristics of said RF receiver coil to alter said RF magnetic field generated by said RF transmission coil.
2. A system according to claim 1, wherein said RF receiver coil couples said magnetic field from said RF receiver coil to said RF transmission coil to adaptively alter said RF magnetic field generated by said RF transmission coil.
3. A system according to claim 1, wherein said RF receiver coil couples said magnetic field from said RF receiver coil to said RF transmission coil to adaptively alter said RF magnetic field generated by said RF transmission coil to refine a field of view imaged by said MR imaging unit.
4. A system according to claim 1, wherein said processor adjusts characteristics of said RF receiver coil by adaptively forming said RF receiver coil into a closed loop including an electrical component.
5. A system according to claim 4, wherein said electrical component comprises at least one of, (a) a capacitor, (b) an inductor and (c) a resistor.
6. A system according to claim 4, wherein said electrical component comprises at least one of, (a) an electrically variable capacitance, (b) an electrically variable inductance and (c) an electrically variable resistance.
7. A system according to claim 4, wherein said electrical component comprises a series combination of at least two of, (a) a capacitor, (b) an inductor and (c) a resistor.
8. A system according to claim 1, wherein said processor adjusts characteristics of said RF receiver coil by connecting an electrical component to said RF receiver coil to form an RF receiver coil having a resonant frequency for coupling a magnetic field from said RF receiver coil to said RF transmission coil to adaptively alter said RF magnetic field generated by said RF transmission coil to a desired field strength.
9. A system according to claim 1, wherein said processor connects an electrical component to said RF receiver coil to select coil resonant frequency for coupling a magnetic field from said RF receiver coil to said RF transmission coil to adaptively alter at least one of, (a) amplitude and (b) phase of said RF magnetic field generated by said RF transmission coil.
10. A system according to claim 1, wherein said adjustment processor determines characteristics required for said RF receiver coil for use in adjusting characteristics of said RF receiver coil.
11. A system according to claim 10, wherein said adjustment processor determines the required characteristics by,
    (a) measuring characteristics including at least one of amplitude and phase of said RF magnetic field generated by said RF transmission coil substantially without coupling a magnetic field from said RF receiver coil to said RF transmission coil,
    (b) comparing the measured characteristics with desired RF magnetic field characteristics to determine a difference in characteristics and
    (c) selecting a resonant frequency of said RF receiver coil to generate a desired RF magnetic field by said RF transmission coil in response to the determined difference in characteristics using predetermined information.
12. A system according to claim 11, wherein said predetermined information comprises predetermined mapping information associating RF receiver coil resonant frequency with corresponding changes in RF transmission coil magnetic field characteristics.
13. A system according to claim 1, including,
    an array of a plurality of RF receiver coils for receiving a plurality of corresponding RF signals for MR image data acquisition and coupling a plurality of corresponding magnetic fields from said plurality of RF receiver coils to said RF transmission coil for adaptively altering said RF magnetic field generated by said RF transmission coil to reduce RF magnetic field inhomogeneity in an imaging region, in response to applying an RF pulse to said RF transmission coil; and
    said adjustment processor adjusts characteristics of first and second RF receiver coils of said plurality of RF receiver coils differently to alter said RF magnetic field to reduce RF magnetic field inhomogeneity.
14. In an MR imaging unit using an RF transmitting coil for generating a Radio Frequency (RF) magnetic field and a plurality of RF receiver coils for receiving RF signals for Magnetic Resonance (MR) image data acquisition, a system for generating a Radio Frequency (RF) magnetic field comprising:
    an RF transmission coil for generating an RF magnetic field;

an array of a plurality of RF receiver coils for receiving a plurality of corresponding RF signals for MR image data acquisition and coupling a plurality of corresponding magnetic fields from said plurality of RF receiver coils to said RF transmission coil for adaptively altering said RF magnetic field generated by said RF transmission coil to reduce RF magnetic field inhomogeneity in an imaging region in response to applying an RF pulse to said RF transmission coil; and an adjustment processor for adjusting characteristics of first and second RF receiver coils of said plurality of RF receiver coils differently, to alter said RF magnetic field to reduce RF magnetic field inhomogeneity.

15. A system according to claim 14, wherein said plurality of RF receiver coils couple said magnetic field from said RF receiver coils to said RF transmission coil to adaptively alter said RF magnetic field generated by said RF transmission coil to refine a field of view imaged by said MR imaging unit.

16. A system according to claim 14, wherein said processor adjusts characteristics of said plurality of RF receiver coils by adaptively forming an individual RF receiver coil into a closed loop including at least one of, (a) a capacitor, (b) an inductor and (c) a resistor.

17. In an MR imaging unit using an RF transmitting coil for generating a Radio Frequency (RF) magnetic field and a plurality of RF receiver coils for receiving RF signals for Magnetic Resonance (MR) image data acquisition, a method for generating a Radio Frequency (RF) magnetic field, comprising the activities of:

generating an RF magnetic field for excitation of protons in MR imaging;

receiving an RF signal for MR image data acquisition and coupling a magnetic field from said RF receiver coil to said RF transmission coil for adaptively altering said RF magnetic field generated by said RF transmission coil to reduce inhomogeneity in said RF magnetic field generated by said RF transmission coil in response to applying an RF pulse to said RF transmission coil; and adjusting characteristics of said RF receiver coil to alter said RF magnetic field generated by said RF transmission coil.

* * * * *